(12) United States Patent
Nakagawa

(10) Patent No.: US 7,318,886 B2
(45) Date of Patent: Jan. 15, 2008

(54) GAS SENSOR HAVING IMPROVED STRUCTURE FOR MINIMIZING THERMAL DAMAGE

(75) Inventor: Kazuya Nakagawa, Kariya (JP)

(73) Assignee: Denso Corporation, Kariya, Aichi-pref. (JP)

( * ) Notice: Subject to any disclaimer, the term of this patent is extended or adjusted under 35 U.S.C. 154(b) by 857 days.

(21) Appl. No.: 10/740,523

(22) Filed: Dec. 22, 2003

(65) Prior Publication Data

US 2004/0129566 A1    Jul. 8, 2004

(30) Foreign Application Priority Data

Dec. 20, 2002    (JP) .............................. 2002-370187

(51) Int. Cl.
*G01N 27/407* (2006.01)
(52) U.S. Cl. .................. 204/428; 204/424; 204/427
(58) Field of Classification Search ................ 204/424, 204/427, 428; 73/23.32; 205/784.5
See application file for complete search history.

(56) References Cited

U.S. PATENT DOCUMENTS

| | | | |
|---|---|---|---|
| 4,323,440 A * | 4/1982 | Akatsuka | 204/428 |
| 5,037,526 A * | 8/1991 | Kato et al. | 204/428 |
| 6,178,806 B1 | 1/2001 | Watanabe et al. | |
| 6,395,159 B2 | 5/2002 | Matsuo et al. | |
| 6,463,788 B2 * | 10/2002 | Nakano et al. | 73/31.05 |

FOREIGN PATENT DOCUMENTS

| | | |
|---|---|---|
| EP | 0918215 A2 | 5/1999 |
| EP | 0899562 A3 | 9/2001 |
| EP | 1167960 A1 | 1/2002 |
| JP | 11-72464 | 3/1999 |

OTHER PUBLICATIONS

French Search Report, date not available.

* cited by examiner

*Primary Examiner*—Kaj K. Olsen
(74) *Attorney, Agent, or Firm*—Nixon & Vanderhye P.C.

(57) ABSTRACT

An improved structure of a gas sensor is provided which is designed to minimize thermal damage to a water-repellent filter installed in a base end portion of the gas sensor. The gas sensor has an elastic seal installed in an opening of the base end portion of the gas sensor and an air cover assembly made up of a main cover and a filter cover. The filter cover is crimped to form at least two necks which establish joints of the filter cover to the main cover through the water-repellent filter. At least one of the necks is used to retain the elastic seal within the main cover. This structure locates the water-repellent filter farther away from the top of the gas sensor exposed to intense heat, thereby minimizing the thermal deformation or deterioration of the water-repellent filter.

5 Claims, 4 Drawing Sheets

GAS SENSOR HAVING IMPROVED STRUCTURE FOR MINIMIZING THERMAL DAMAGE

BACKGROUND OF THE INVENTION

1. Technical Field of the Invention

The present invention relates generally to a gas sensor which may be installed in an exhaust pipe of automotive engines to measure the concentration of gas such as $O_2$, NOx, or CO, and more particularly to an improved structure of such a gas sensor which is designed to minimize thermal damage to a water-repellent filter.

2. Background Art

Gas sensors are known which are installed in an exhaust pipe of automotive vehicles for use in air-fuel ratio control of engines.

FIG. 7 shows one example of such a type of gas sensor which is taught in Japanese Patent First Publication No. 11-72464 (corresponding to U.S. Pat. No. 6,395,159 B2, issued May 28, 2002).

The gas sensor 9 includes a gas sensor element working to measure the concentration of a given component contained in gasses, a housing within which the gas sensor element is disposed through an insulation porcelain, a gas sensor element protective cover joined to a top end of the housing, and an atmosphere side cover 91 joined to a base end of the housing.

The atmosphere side cover 91 is made up of a main cover 911 and a filter cover 912. The main cover 911 includes a large-diameter portion which is exposed to air and welded to a side wall of the base end of the housing and a small-diameter portion surrounded by the filter cover 912. The filter cover 912 is crimped to form necks which works to joint the filter cover 912 to the small-diameter portion of the main cover 911 through a cylindrical water-repellent filter 23.

An elastic seal 17 is installed hermetically within an open end of the small-diameter portion of the main cover 911. The elastic seal 17 is retained firmly, as clearly shown in the drawing, through the necks of the main cover 911 and the filter cover 912. Leads 16 extend hermetically through holes 170 formed in the elastic seal 17 outside the gas sensor 9 for transmitting a sensor output to and receiving electric power from an external sensor controller.

When the gas sensor 19 is installed in the exhaust pipe of the automotive engine, a top end portion (not shown) of the housing is exposed to the exhaust gasses, so that it is exposed to intense heat. The heat is transmitted to the atmosphere side cover 91, thus causing a top end portion of the main cover 911 to be elevated in temperature. The main cover 911 is, as described above, exposed to air, so that the temperature thereof drops gradually from the top end portion to a base end portion thereof (i.e., an upper portion, as viewed in the drawing).

The small-diameter portion of the main cover 911 is surrounded by the water-repellent filter 23 and the filter cover 912, so that the heat stays at the small-diameter portion.

The water-repellent filter 23 is usually made of a porous resin material, so that it may, like the elastic seal 171, undergo a thermal deformation or a change in coefficient of elasticity, thus causing the joint of the water-repellent filter 23 to the main cover 911 to be loosened. The thermal deformation of the water-repellent filter 23 also causes pores thereof to be occluded or closed, thus resulting in disturbance of a flow of the air from outside the filter cover 912 to inside the main cover 911 through air vents 913 and 914. This results in a lack of oxygen within the gas sensor 9, which leads to a failure in operation of the gas sensor 9.

SUMMARY OF THE INVENTION

It is therefore a principal object of the present invention to avoid the disadvantages of the prior art.

It is another object of the present invention to provide an improved structure of a gas sensor which provides a portion of the gas sensor around a water-repellent filter which is less sensitive to heat.

According to one aspect of the invention, there is provided a gas sensor which may be installed in an exhaust pipe of automotive engines to measure the concentration of a given component of exhaust gasses of the engine. The gas sensor has a length with a first end and a second end opposed to the first end and comprises: (a) a hollow cylindrical housing having a first end facing the first end of the gas sensor and a second end facing the second end of the gas sensor; (b) a sensor element disposed within the housing, the sensor element having a base portion projecting from the first end of the housing and a sensing portion projecting from the second end of the housing, the sensing portion working to measure a concentration of a given component of gasses; (c) a cylindrical measurement side cover joined to the second end of the housing to define a gas chamber which is filled with the gasses and to which the sensing portion of the sensor element is exposed; (d) an elastic seal; (e) a cylindrical water-repellent filter; (f) a cylindrical atmosphere side cover assembly joined to the housing to define an air chamber to which the base portion of the sensor element is exposed; and (g) air vents. The atmosphere side cover assembly includes a main cover and a filter cover. The main cover has a first end facing the first end of the gas sensor and a second end facing the second end of the gas sensor and is joined at the second end thereof to the first end of the housing. The main cover has a first end portion which is crimped to form a first neck working to retain the elastic seal within the first end portion. The filter cover is crimped to form a second neck closer to the first end of the main cover than the first neck and a third neck closer to the second end of the main cover than the first neck. The second and third necks establish joints of the filter cover to an outer side wall of the first end portion of the main cover through the water-repellent filter and define a cavity therebetween around the first neck of the main cover within which the water-repellent filter is disposed. The air vents are formed in the main cover and the filter cover of the atmosphere side cover assembly which face the water-repellent filter disposed within the cavity. The air vents work to create a flow of air from outside the atmosphere side cover assembly to inside the air chamber through the water-repellent filter.

As already discussed in the introductory part of this application, in the case where the gas sensor is installed in the exhaust pipe of the engine, the top of the gas sensor is heated by exhaust gasses flowing in the exhaust pipe, so that the housing is elevated in temperature. The above structure retains the water-repellent filter at a location where it faces the elastic seal. In other words, the water-repellent filter is located farther away from the top of the gas sensor exposed to intense heat than the conventional structure, as illustrated in FIG. 7, thereby resulting in a decreased rise in temperature of the water-repellent filter, which minimizes thermal deformation or deterioration of the water-repellent filter.

The formation of the first neck on the main cover facilitates ease of forming the larger volume cavity between the main cover and the filter cover within which the water-repellent filter is disposed. The air vents and are formed inside and outside the water-repellent filter in the main cover and the filter cover. This structure facilitates flow of air from outside the filter cover toward the main cover.

In the preferred mode of the invention, the air vent of the main cover of the atmosphere side cover assembly has an end closer to the second end of the main cover than an end of the elastic seal, thereby facilitating the flow of air into the air chamber.

The main cover of the atmosphere side cover assembly is made of a material which is higher in hardness than that of the filter cover.

According to the second aspect of the invention, there is provided a gas sensor which has a length with a first end and a second end opposed to the first end. The gas sensor comprises: (a) a hollow cylindrical housing having a first end facing the first end of the gas sensor and a second end facing the second end of the gas sensor; (b) a sensor element disposed within the housing, the sensor element having a base portion projecting from the first end of the housing and a sensing portion projecting from the second end of the housing, the sensing portion working to measure a concentration of a given component of gasses; (c) a cylindrical measurement side cover joined to the second end of the housing to define a gas chamber which is filled with the gasses and to which the sensing portion of the sensor element is exposed; (d) an elastic seal; (e) a cylindrical water-repellent filter; (f) a cylindrical atmosphere side cover assembly joined to the housing to define an air chamber to which the base portion of the sensor element is exposed; and (g) air vents. The atmosphere side cover assembly includes a main cover and a filter cover. The main cover has a first end facing the first end of the gas sensor and a second end facing the second end of the gas sensor and is joined at the second end thereof to the first end of the housing. The filter cover is crimped to form a first neck closer to the first end of the main cover and a second neck closer to the second end of the main cover. The first and second necks establish a first and a second joint of the filter cover to an outer wall of the main cover, respectively, and define a cavity therebetween within which the water-repellent filter is disposed. The first joint works to retain the elastic seal within the main cover. The second joint works to retain the water-repellent filter in the cavity along with the first joint. The air vents are formed in the main cover and the filter cover of the atmosphere side cover assembly which face the water-repellent filter disposed within the cavity. The air vents work to create a flow of air from outside the atmosphere side cover assembly to inside the air chamber through the water-repellent filter. This structure retains the water-repellent filter at a location where it faces the elastic seal. In other words, the water-repellent filter is located farther away from the top of the gas sensor exposed to intense heat than the conventional structure, as illustrated in FIG. 7, thereby resulting in a decreased rise in temperature of the water-repellent filter, which minimizes thermal deformation or deterioration of the water-repellent filter.

In the preferred mode of the invention, the main cover of the atmosphere side cover assembly is made of a material which is higher in harness than that of the filter cover.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
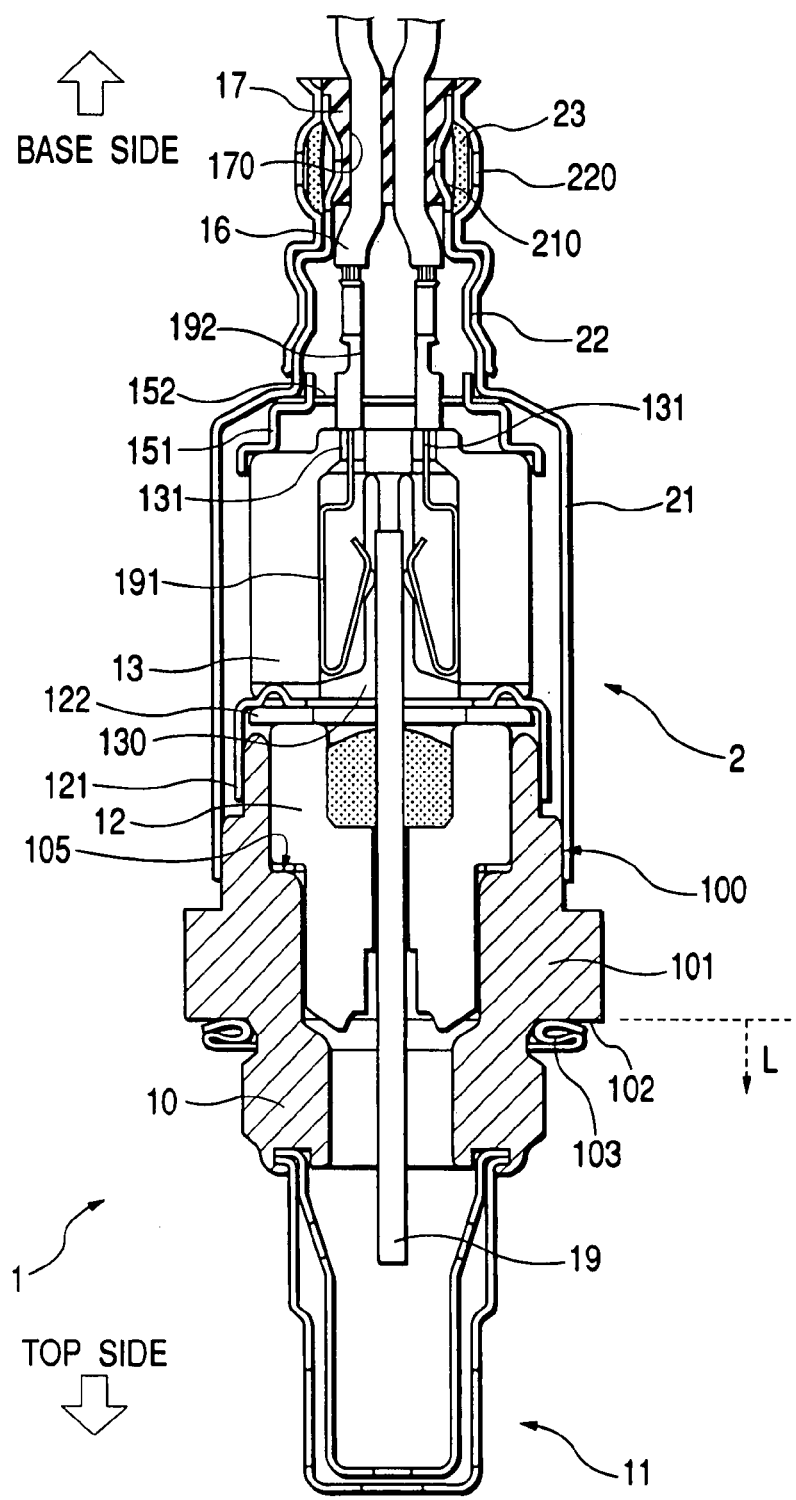
FIG. 1 is a longitudinal sectional view which shows a gas sensor according to the first embodiment of the invention.

Referring now to the drawings, wherein like numbers refer to like parts in several views, particularly to FIG. 1, there is shown a gas sensor 1 according to the first embodiment of the invention which may be employed in automotive air-fuel ratio control systems to measure $O_2$, HC, CO, or NOx contained in exhaust gasses of an internal combustion engine. The gas sensor 1 may also be installed in an exhaust pipe of automotive engines and work as an air-fuel ration sensor.

The gas sensor 1 generally includes a hollow cylindrical housing 10, a sensor element 19 disposed within the housing 10, a double-walled protective cover assembly 3 secured to a head end of the housing 10 to cover a sensing portion of the gas sensor element 19, and a hollow cylindrical air cover 2 joined to a base end of the housing 10. The sensor element 19 works to output a signal as a function of the concentration of a given component of gasses.

The sensor element 19 may be made of a laminated plate such as one taught in U.S. Pat. No. 5,573,650, issued Nov. 12, 1996 to Fukaya et al., disclosure of which is incorporated herein by reference. The gas sensor element 19 may alternatively be made of a known cup-shaped sensor element.

The air cover 2 is made up of a cylindrical main cover 21 and a cylindrical filter cover 22. The main cover 21 is welded directly to a side wall of a base portion of the housing 10. The filter cover 22 is secured to an outer surface of a small-diameter portion of the main cover 21 and crimped to retain a water-repellent filter 23 on the periphery of the main cover 21. The main cover 21 and the filter cover 22 have formed therein air vents 210 and 220 through which air is admitted into the air chamber defined inside the small-diameter portion of the main cover 21. The air vents 210 and 220 face the water-repellent filter 23.

An elastic seal 17 is retained firmly within an open base end of the main cover 21 to create an air-tight seal in the base end of the main cover 21. The retaining of the elastic seal 17 is achieved, as clearly shown in FIG. 2, by crimping a base end portion (i.e., the small-diameter portion) of the main cover 21 to form a first annular shriveled portion 251 which will also be referred to as a neck below. The first neck 251 has an outer surface facing the water-repellent filter 23.

The filter cover 22 is joined to the base end portion of the main cover 21 by crimping it to form second and third annular shriveled portions 252 and 253 which will also be referred to as necks below. The second neck 252 is located closer to the base end of the filter cover 22 than the first neck 251, while the third neck 253 is located closer to a top end (i.e., a lower side, as viewed in FIG. 2) of the filter cover 22 than the first neck 251. Specifically, the second and third necks 252 and 253 are located out of coincidence with the first neck 251 in a radius direction of the air cover 2.

The gas sensor 1 is installed, for example, in a wall of an exhaust pipe joining to the automotive engine to determine an air-fuel ratio for use in air-fuel ratio control of the engine. In the installation of the gas sensor 1, an end surface 102 of a flange 100 of the housing 10, as illustrated in FIG. 1, is placed in abutment to an outer surface of the wall of the exhaust pipe through a spring 103. The spring 103 works to provide hermetic sealing between the end surface 102 and the outer surface of the exhaust pipe.

When the engine is running, a lower portion of the gas sensor 1 below a broken line L in FIG. 1, is exposed to exhaust gasses flowing within the exhaust pipe and heated thereby. An upper portion of the gas sensor 1 above the broken line L is exposed to the atmospheric air. The temperature of the gas sensor 1, thus, decreases gradually from the broken line L to the base end of the gas sensor 1 (i.e., the upper end, as viewed in FIG. 1).

The protective cover assembly 11 is of a double-walled structure and made up of an outer cylindrical cover and an inner cylindrical cover disposed within the outer cover coaxially with each other. The outer and inner covers have gas holes through which the exhaust gasses pass and enter inside a gas chamber defined in the inner cover. The gas sensor 1 has a head portion (i.e., the sensing portion) exposed to the exhaust gasses in the inner cover. The protective cover assembly 11 may alternatively be of a single- or multi-walled (more than two) structure.

The sensor element 19 is retained within the housing 10 through a cylindrical insulation porcelain 12. Gas-tight seals are formed between the insulation porcelain 12 and the housing 10 and between the insulation porcelain 12 and the sensor element 19.

An annular disc spring 122 is disposed on a base end of the insulation porcelain 12 and covered with a press cup 121. The press cup 121 is so fitted on a side wall of the housing 10 as to press the disc spring 122. The disc spring 122, thus, produces a reactive force oriented in a direction parallel to a longitudinal center line of the gas sensor 1 which urges the insulation porcelain 12 into constant engagement with a tapered inner shoulder 105 of the housing 10.

A hollow cylindrical insulation porcelain 13 is mounted on the press cup 121. The insulation porcelain 13 has an inner cavity 130 to which a base portion of the sensor element 19 is exposed. The insulation porcelain 13 has formed in a base end thereof holes 131 which establish communication between the inner cavity 130 and the atmosphere.

The sensor element 19 connects with leads 16 through terminals 191 and connectors 192 such as clamp contacts for transmitting an output of the sensor element 19 to and receiving electric power from an external sensor controller (not shown). The terminals 191 pass through the holes 131 and extend into an air chamber formed inside a base portion of the air cover 2 above the insulation porcelain 13. Within the air chamber, the terminals 191 are joined electrically to the leads 16 through the connectors 192.

A cylindrical press cup 151 is fitted on a shoulder of the base end of the insulation porcelain 13 and urged by an inner shoulder of the main cover 21 downward. An annular plate 152 is installed on a base end of the press cup 151 which works to apply pressures to the base end of the press cup 151 inwardly in a radius direction of the press cup 151 to hold the base end from expanding outward. The press cup 151 and the annular plate 152 work to hold the insulation porcelain 13 firmly within the air cover 2 without any play.

Figure 2:
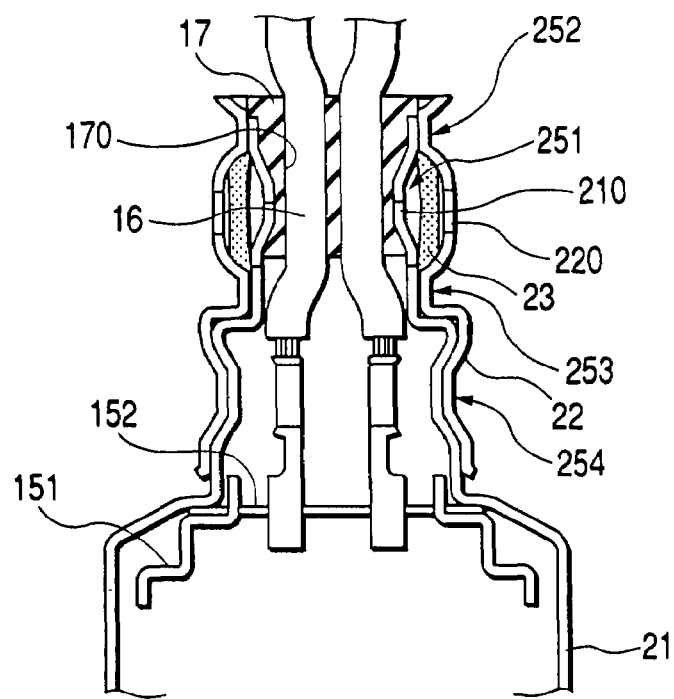
FIG. 2 is a partially enlarged sectional view which shows installation of an elastic seal and a water-repellent filter in a gas sensor in the first embodiment.

The air cover 2 is, as clearly shown in FIG. 2, made up of the main cover 21 and the filter cover 22 crimped to hold the water-repellent filter 23 between itself and the base end portion of the main cover 22. The main cover 21 and the filter cover 22 are made of cylindrical stainless steel (e.g., SUS304). The main cover 21 has a Vickers hardness of 230. The filter cover 22 has a Vickers hardness of 140.

The water-repellent filter 23 is made of a porous material such as tetrafluoroethylene which has higher air permeability. The main cover 21 is made up of the small-diameter portion and the large-diameter portion which is welded directly, as shown in FIG. 1, to the side wall 100 of the housing 10.

The elastic seal 17 is installed in the open end of the main cover 21 in elastic abutment with an inner wall of a portion of a lap of the main cover 21 and the filter cover 22. The installation is, as described above, achieved by crimping the base end portion of the main cover 21 to grasp the elastic seal 17 elastically at the first neck 251.

The filter cover 22 is fitted on the base end portion of the main cover 21 outside the first neck 251 and jointed to the outer wall of the main cover 21 at the second and third necks 252 and 253 located across the first neck 251. The joining of the filter cover 22 to the main cover 21 is achieved by putting a hollow cylinder of uniform diameter on the base end portion (i.e., the small-diameter portion) of the main cover 21 and crimping it to form a neck 254 in addition to the second and third necks 252 and 253.

The main cover 21 and the filter cover 22 have formed therein the air vents 210 and 220 through which air is admitted into the air chamber defined inside the small-diameter portion of the main cover 21. The air vents 210 are located at regular intervals around the first neck 251 of the main cover 21. Similarly the air vents 220 are located at regular intervals around the filter cover 22. The air vents 210 and 220 face the water-repellent filter 23.

Each of the air vents 201 of the main cover 21 extends vertically, as viewed in the FIGS. 1 and 2, to have a top end (i.e., a lower end as viewed in the drawings) located closer to the top end of the gas sensor 1 than the top end surface (i.e. a lower end surface as viewed in the drawings) of the elastic seal 17, thereby establishing communication between the air vents 220 and the air chamber within the main cover 21 through the water-repellent filter 23. Specifically, the air entering the air vents 220 of the filter cover 22 passes through the water-repellent filter 23 and the first neck 251 (i.e., the air vents 210), thereby forming an air flow oriented diagonally down to inside the main cover 21 (i.e., the air chamber) from the air vents 220 of the filter cover 22.

Crimping of the main cover 21 and the filter cover 22 is accomplished in the following steps.

Figure 3:
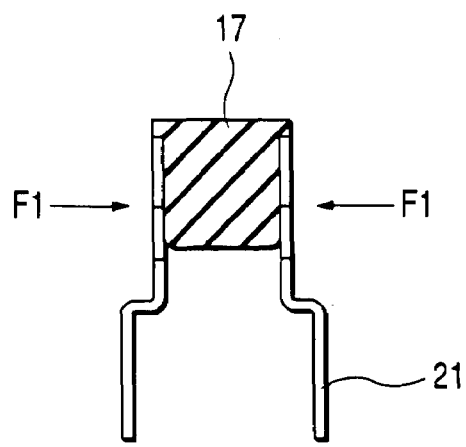
FIG. 3 is a partially sectional view which shows a production step of crimping an air cover to retain an elastic seal.
Figure 4:
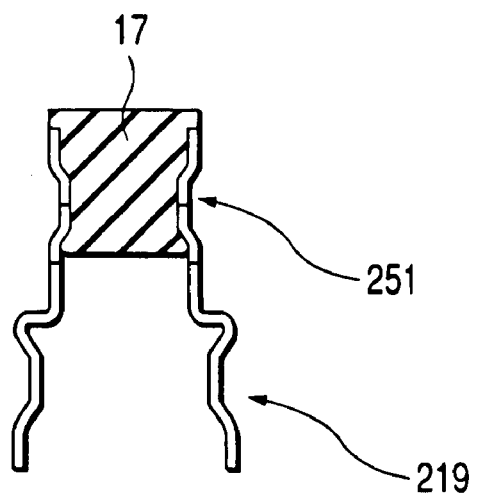
FIG. 4 is a partially sectional view which shows a second production step following the step as illustrated in FIG. 3.

First, the elastic seal 17 is, as shown in FIG. 3, put in the open end of the main cover 21. The pressure F1 is applied to the periphery of a smaller-diameter portion of the main cover 21 in a radius direction of the main cover 21 to shrivel the side wall to form, as shown in FIG. 4, the first neck 251.

Simultaneously, pressure is applied to a larger-diameter portion of the main cover 21 to shrivel it to form a neck 219.

Next, the water-repellent filter 23 and the filter cover 22 are fitted on the smaller-diameter portion of the main cover 21 in abutment of a lower end of the water-repellent filter 23 and an inner shoulder of the filter cover 22 with a shoulder of the main cover 21 formed above the neck 219. Specifically, the water-repellent filter 23 is placed around the elastic seal 7.

Figure 5:
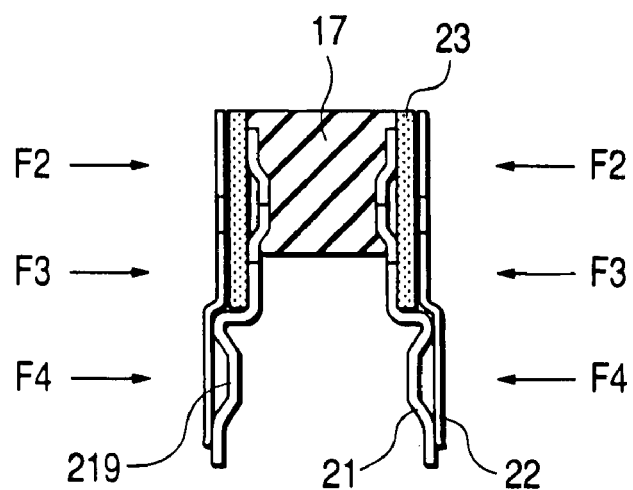
FIG. 5 is a partially sectional view which shows a third production step following the step as illustrated in FIG. 4.

Finally, pressures F2, F3, and F4 are, as shown in FIG. 5, applied to the side wall of the filter cover 22 to form the necks 252, 253, and 254, as illustrated in FIG. 2, thereby establishing a firm joint of the filter cover 22 to the main cover 21 and retaining the elastic seal 17 within the open end of the main cover 21 hermetically.

Figure 7:
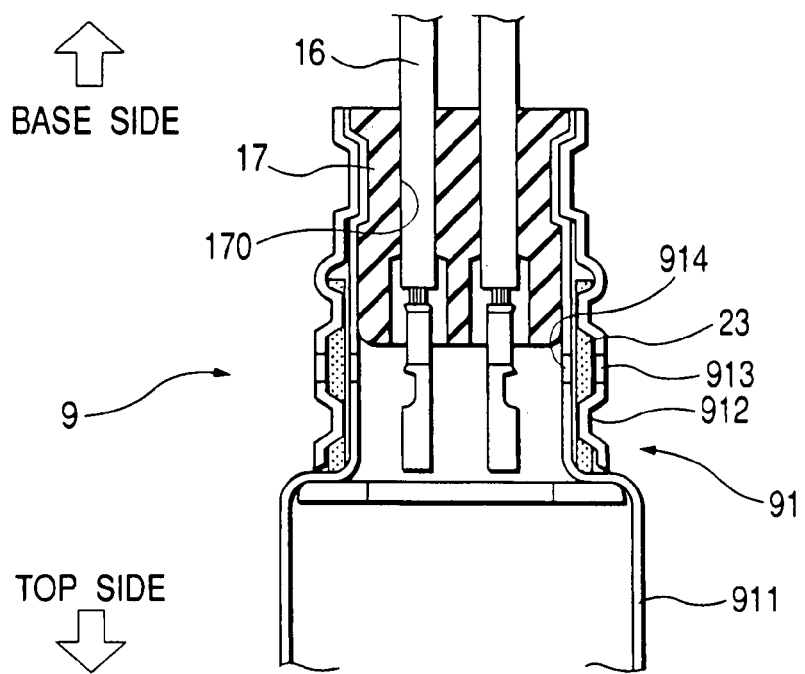
FIG. 7 is a partially enlarged sectional view which shows installation of an elastic seal and a water-repellent filter in a conventional gas sensor.

As apparent from the above discussion, firm fixing of the elastic seal 17 within the open end of the main cover 21 is achieved by forming the first neck 251 on the main cover 21. The firm joint of the filter cover 22 to the main cover 21 is achieved by forming the second and third necks 252 and 253 on the filter cover 22. The water-repellent filter 23 is placed around the first neck 251 and retained by the second and third necks 253 and 253. Specifically, the water-repellent filter 23 is disposed at a location where it faces the elastic seal 17. In other words, the water-repellent filter 23 is located farther away from the top end of the gas sensor 1 exposed to intense heat than the conventional structure, as illustrated in FIG. 7, thereby resulting in a decreased rise in temperature of the water-repellent filter 23, which minimizes thermal deformation or deterioration of the water-repellent filter 23.

The formation of the first neck 251 on the main cover 21 facilitates ease of forming a larger volume cavity between the main cover 21 and the filter cover 22 within which the water-repellent filter 23 is disposed. The air vents 210 and 220 are formed inside and outside the water-repellent filter 23 in the main cover 21 and the filter cover 22. This structure facilitates flow of air from outside the filter cover 22 toward the main cover 21.

Each of the air vents 201 of the main cover 21 extends vertically, as viewed in the FIGS. 1 and 2, to have the top end located closer to the top end of the gas sensor 1 than the top end surface of the elastic seal 17, thereby creating a flow of a required amount of air to inside the main cover 21.

Figure 6:
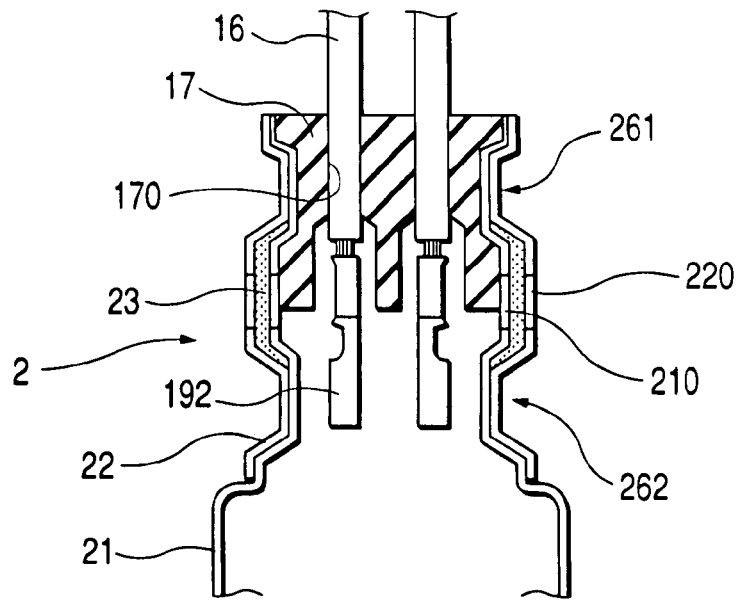
FIG. 6 is a partially enlarged sectional view which shows installation of an elastic seal and a water-repellent filter in a gas sensor according to the second embodiment of the invention.

FIG. 6 shows the gas sensor 1 according to the second embodiment of the invention.

The air cover 2 consists of the main cover 21 joined to the base end of the housing 10 (not shown in FIG. 6) and the filter cover 22 joined to the base end portion of the main cover 21 through the cylindrical water-repellent filter 23.

The air vents 210 of the main cover 21 coincide with the air vents 220 of the filter cover 22 through the water-repellent filter 23.

The main cover 21 and the filter cover 22 have upper necks 261 and lower necks 262. The upper necks 261 work to retain the elastic seal 17 firmly within the open end of the main cover 21 and also join the filter cover 22 to the main cover 21 firmly together with the lower necks 262. The upper and lower necks 261 and 262 also work to hold the water-repellent filter 23 therebetween.

The water-repellent filter 23 is, like the first embodiment, disposed at a location where it faces the elastic seal 17. In other words, the water-repellent filter 23 is located farther away from the top end of the gas sensor 1 exposed to intense heat than the conventional structure, as illustrated in FIG. 7, thereby resulting in a decreased rise in temperature of the water-repellent filter 23, which minimizes thermal deformation or deterioration of the water-repellent filter 23.

Other arrangements are identical with those in the first embodiment, and explanation thereof in detail will be omitted here.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor having a length with a first end and a second end opposed to the first end comprising:
   a hollow cylindrical housing having a first end facing the first end of the gas sensor and a second end facing the second end of the gas sensor;
   a sensor element disposed within said housing, said sensor element having a base portion projecting from the first end of said housing and a sensing portion projecting from the second end of said housing, the sensing portion working to measure a concentration of a given component of gasses;
   a cylindrical measurement side cover joined to the second end of said housing to define a gas chamber which is filled with the gasses and to which the sensing portion of said sensor element is exposed;
   an elastic seal;
   a cylindrical water-repellent filter;
   a cylindrical atmosphere side cover assembly joined to said housing to define an air chamber to which the base portion of said sensor element is exposed, said atmosphere side cover assembly including a main cover and a filter cover, the main cover having a first end facing the first end of the gas sensor and a second end facing the second end of the gas sensor and being joined at the second end thereof to the first end of said housing, the main cover having a first end portion which is crimped to form a first neck working to retain said elastic seal within the first end portion, the filter cover being crimped to form a second neck closer to the first end of the main cover than the first neck and a third neck closer to the second end of the main cover than the first neck, the second and third necks establishing joints of the filter cover to an outer side wall of the first end portion of the main cover through said water-repellent filter and defining a cavity therebetween around the first neck of the main cover within which said water-repellent filter is disposed; and
   air vents formed in the main cover and the filter cover of said atmosphere side cover assembly which face said water-repellent filter disposed within the cavity, said air vents working to create a flow of air from outside said atmosphere side cover assembly to inside the air chamber.

2. A gas sensor as set forth in claim 1, wherein the air vent of the main cover of said atmosphere side cover assembly has an end closer to the second end of the main cover than an end of said elastic seal.

3. A gas sensor as set forth in claim 1, wherein the main cover of said atmosphere side cover assembly is made of a material which is higher in hardness than that of the filter cover.

4. A gas sensor having a length with a first end and a second end opposed to the first end comprising:
- a hollow cylindrical housing having a first end facing the first end of the gas sensor and a second end facing the second end of the gas sensor;
- a sensor element disposed within said housing, said sensor element having a base portion projecting from the first end of said housing and a sensing portion projecting from the second end of said housing, the sensing portion working to measure a concentration of a given component of gasses;
- a cylindrical measurement side cover joined to the second end of said housing to define a gas chamber which is filled with the gasses and to which the sensing portion of said sensor element is exposed;
- an elastic seal;
- a cylindrical water-repellent filter;
- a cylindrical atmosphere side cover assembly joined to said housing to define an air chamber to which the base portion of said sensor element is exposed, said atmosphere side cover assembly including a main cover and a filter cover, the main cover having a first end facing the first end of the gas sensor and a second end facing the second end of the gas sensor and being joined at the second end thereof to the first end of said housing, the filter cover being crimped to form a first neck closer to the first end of the main cover and a second neck closer to the second end of the main cover, the first and second necks establishing a first and a second joint of the filter cover to an outer wall of the main cover, respectively, and defining a cavity therebetween within which said water-repellent filter is disposed, the first joint working to retain the elastic seal within the main cover, the second joint working to retain said water-repellent filter in the cavity along with the first joint; and
- air vents formed in the main cover and the filter cover of said atmosphere side cover assembly which face said water-repellent filter disposed within the cavity, said air vents working to create a flow of air from outside said atmosphere side cover assembly to inside the air chamber.

5. A gas sensor as set forth in claim 4, wherein the main cover of said atmosphere side cover assembly is made of a material which is higher in hardness than that of the filter cover.

* * * * *